(12) United States Patent
Muthusamy et al.

(10) Patent No.: US 12,043,597 B2
(45) Date of Patent: Jul. 23, 2024

(54) CRYSTALLINE POLYMORPHS OF RIVOCERANIB AND RIVOCERANIB MESYLATE

(71) Applicant: ASSIA CHEMICAL INDUSTRIES LTD., Petach Tikva (IL)

(72) Inventors: Anantha Rajmohan Muthusamy, Sivakasi (IN); Sundara Lakshmi Kanniah, Vellore (IN); Elluru Subbireddy, Greater Noida (IN)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 58 days.

(21) Appl. No.: 17/874,399

(22) Filed: Jul. 27, 2022

(65) Prior Publication Data

US 2022/0371998 A1    Nov. 24, 2022

Related U.S. Application Data

(63) Continuation of application No. 17/269,290, filed as application No. PCT/US2019/049434 on Sep. 4, 2019, now Pat. No. 11,434,202.

(30) Foreign Application Priority Data

Sep. 5, 2018 (IN) .............................. 201811033405
Oct. 17, 2018 (IN) .............................. 201811039438
Jun. 4, 2019 (IN) .............................. 201911022155

(51) Int. Cl.
C07D 213/82 (2006.01)

(52) U.S. Cl.
CPC ........ C07D 213/82 (2013.01); C07B 2200/13 (2013.01)

(58) Field of Classification Search
CPC .................................................. C07D 213/82
USPC .......................................................... 514/332
See application file for complete search history.

(56) References Cited

U.S. PATENT DOCUMENTS

| 6,627,646 B2 | 9/2003 | Bakale et al. |
| 9,988,355 B2 * | 6/2018 | Yu .......................... A61P 35/00 |
| 2011/0184023 A1 | 7/2011 | Yuan et al. |

FOREIGN PATENT DOCUMENTS

| CN | 104072410 A | 10/2014 |
| CN | 104072411 A | 10/2014 |
| CN | 104086483 A | 10/2014 |
| CN | 105017142 A | 11/2015 |
| CN | 105801476 A | 7/2016 |

OTHER PUBLICATIONS

International Search Report and Written Opinion of the International Searching Authority issued in correspong Appl. No. PCT/US2019/049434 mailed Oct. 28, 2019 (14 pages).
Muzaffar et al., "Polymorphism and Drug Availability, etc.," J of Pharm. (Lahore), 1979, 1 (1 ), 59-66.
U.S. Pharmacopia#23, National Formulary#18, 1995, 1843-1844.
Doelker, english translation of S. T. P, Pratiques ( 1999), 9(5), 399-409, pp. 1-33.
Doelker, english translation of Ann. Pharm. Fr., 2002, 60: 161-176, pp. 1-39.
Taday et al., "Using Terahertz, etc.," J of Pharm. Sci., 92(4), 2003, 831-838.
Otuska et al., "Effect of Polymorphic, etc.," Chem. Pharm. Bull., 47(6) 852-856 (1999).
Guillory (in Brittain ed.), Polymorphism in Pharmaceutical Solids, NY: Marcel Dekker., 1-2, 183-226. (Year: 1999).
Rodriguez-Spong et al., "General principles, etc.," Adv. Drug Delivery REviews 56 241-27 4. (Year: 2004).
CMU Pharmaceutical polymorphism, internet p. 1-3 (2002) printout Apr. 3, 2008.
Singhal et al., "Drug Polymorphism, etc.," Advanced Drug Delivery reviews 56, p. 335-347 (2004).
Concise Encyclopedia Chemistry, NY: Walter de Gruyter, 1993, 872-873.
Jain et al., "Polymorphism in Pharmacy", Indian Drugs, 1986, 23(6) 315-329.

* cited by examiner

*Primary Examiner* — Taofiq A Solola
(74) *Attorney, Agent, or Firm* — Carter, DeLuca & Farrell LLP

(57) ABSTRACT

The present disclosure encompasses crystalline polymorphs of Rivoceranib and Rivoceranib mesylate (Apatinib mesylate), processes for preparation thereof, and pharmaceutical compositions thereof.

3 Claims, 11 Drawing Sheets

A characteristic X-ray powder diffraction pattern (XRPD) of Rivoceranib Form RT1.

A characteristic X-ray powder diffraction pattern (XRPD) of Rivoceranib mesylate Form RT2.

A Characteristic X-ray powder diffraction pattern (XRPD) of Rivoceranib mesylate Form A, as disclosed in US patent No. 9,988,355 (figure 1).

A Characteristic X-ray powder diffraction pattern (XRPD) of Rivoceranib Form D, as disclosed in patent publication CN104072410 (figure 1).

A characteristic X-ray powder diffraction pattern (XRPD) of Rivoceranib Form RT3

A characteristic X-ray powder diffraction pattern (XRPD) of Rivoceranib mesylate Form RT4.

A characteristic X-ray powder diffraction pattern (XRPD) of Rivoceranib Form B, as disclosed in CN105017142 (figure 1).

A characteristic X-ray powder diffraction pattern (XRPD) of Rivoceranib mesylate Form RT5.

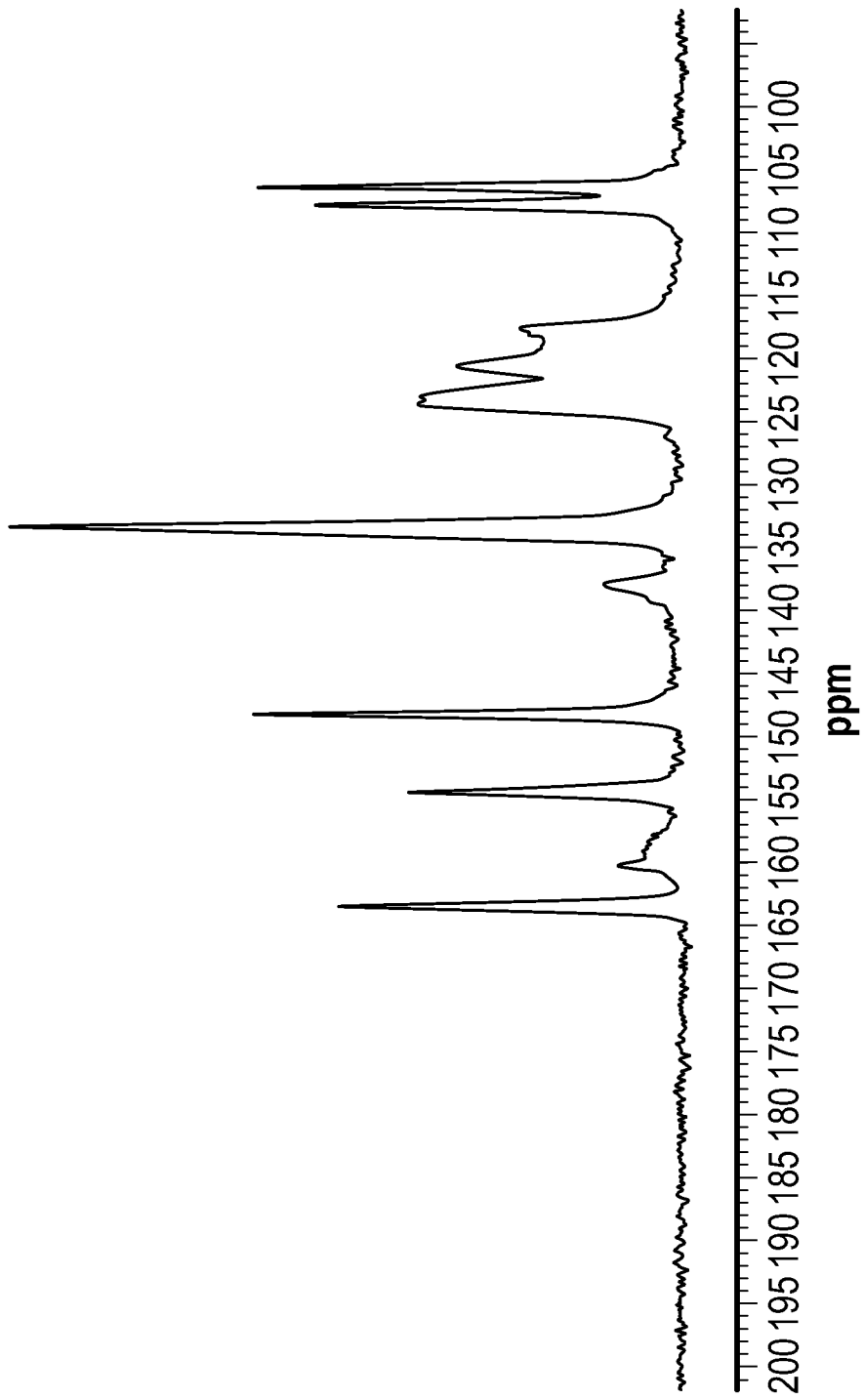

CRYSTALLINE POLYMORPHS OF RIVOCERANIB AND RIVOCERANIB MESYLATE

CROSS REFERENCE TO RELATED APPLICATIONS

This application is a continuation of U.S. application Ser. No. 17/269,290 filed Feb. 18, 2021, which is a National Stage Application of, and claims priority to and the benefit of, International Patent Application No. PCT/US2019/049434 filed on Sep. 4, 2019, which, in turn, claims the benefit of, and priority to, Indian Provisional Application No. 201811033405 filed Sep. 5, 2018, Indian Provisional Application No. 201811039438 filed Oct. 17, 2018, and Indian Provisional Application No. 201911022155 filed Jun. 4, 2019, the entire disclosures of each of which are incorporated by reference herein.

FIELD OF THE INVENTION

The present disclosure encompasses crystalline polymorphs of Rivoceranib and Rivoceranib mesylate (Apatinib mesylate), processes for preparation thereof, and pharmaceutical compositions thereof.

BACKGROUND OF THE INVENTION

Rivoceranib mesylate, also known as Apatinib mesylate, has the chemical name N-[4-(1-Cyanocyclopentyl)phenyl]-2-(pyridin-4-ylmethylamino)pyridine-3-carboxamide methanesulfonate and having the following chemical structure:

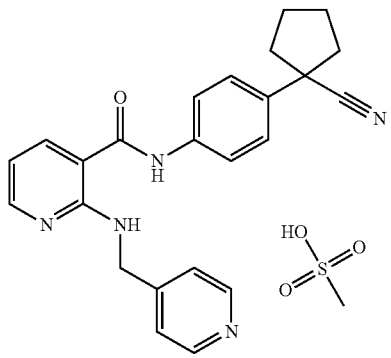

Rivoceranib mesylate is a molecularly targeted antitumor drug and is a typical small molecule vascular endothelial growth factor tyrosine kinase inhibitor that can be used to treat advanced non-small cell lung cancer, gastric cancer, liver cancer, breast cancer and other types of cancer. Rivoceranib compound is first described in U.S. Pat. No. 7,129,252. Rivoceranib mesylate process is described in U.S. Pat. No. 8,362,256 (example 4) by obtaining product having a melting point of 193.5-195° C. Polymorphs of Rivoceranib mesylate are described in U.S. Pat. No. 9,988,355 (form A) and other polymorphs of Rivoceranib are described in the following patent publications: CN105017142 (Form B), CN104072411 (Form C), CN104072410 (Form D), CN104086483 (Form F) and CN105801476 (Form II).

Polymorphism, the occurrence of different crystalline forms, is a property of some molecules and molecular complexes. A single molecule, like Rivoceranib, may give rise to a variety of polymorphs having distinct crystal structures and physical properties like melting point, thermal behaviors (e.g., measured by thermogravimetric analysis—"TGA", or differential scanning calorimetry—"DSC"), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Rivoceranib and Rivoceranib mesylate.

SUMMARY OF THE DISCLOSURE

The present disclosure provides crystalline polymorphs of Rivoceranib and Rivoceranib mesylate, processes for preparation thereof and pharmaceutical compositions thereof.

The present disclosure also provides uses of the polymorphs of Rivoceranib and Rivoceranib mesylate for preparing other solid state forms of Rivoceranib or Rivoceranib mesylate or other Rivoceranib salts and solid state forms thereof.

In embodiments, the present disclosure relates to solid state forms of Rivoceranib mesylate designated as Form RT2, Form RT4 and Form RT5 and solid states forms of Rivoceranib Form RT1 and Form RT3 (defined herein). The present disclosure also provides the uses of any one or combination of the described solid state forms of Rivoceranib and Rivoceranib mesylate for preparing other solid state forms of Rivoceranib and Rivoceranib mesylate or other salts of Rivoceranib and their solid state forms thereof.

The present disclosure further provides processes for preparing other solid state forms of Rivoceranib or Rivoceranib mesylate or other salts of Rivoceranib and solid state forms thereof.

In another embodiment, the present disclosure provides any one of the above described crystalline polymorphs of Rivoceranib and Rivoceranib mesylate for use in medicine, in embodiments for the treatment of cancer.

The present disclosure also encompasses the uses of any one of the described crystalline polymorphs of Rivoceranib and Rivoceranib mesylate for the preparation of pharmaceutical compositions and/or formulations.

In another aspect, the present disclosure provides pharmaceutical compositions including any one of the crystalline polymorphs of Rivoceranib or Rivoceranib mesylate according to the present disclosure.

In yet another embodiment, the present disclosure encompasses pharmaceutical formulations including any one or combination of the described crystalline polymorphs of Rivoceranib and Rivoceranib mesylate and at least one pharmaceutically acceptable excipient.

The present disclosure includes processes for preparing said pharmaceutical formulations of Rivoceranib and Rivoceranib mesylate including combining any one or combination of the described crystalline polymorphs and at least one pharmaceutically acceptable excipient.

The present disclosure further provides the crystalline polymorphs defined herein as well as the pharmaceutical compositions or formulations of the crystalline polymorphs of Rivoceranib and Rivoceranib mesylate as medicaments, in embodiments for the treatment of cancer.

The present disclosure also provides methods of treating cancer, by administering a therapeutically effective amount of any one or combination of the crystalline polymorphs of Rivoceranib and Rivoceranib mesylate of the present disclosure, or at least one of the herein described pharmaceutical compositions or formulations, to a subject suffering from cancer, or otherwise in need of the treatment.

The present disclosure also provides uses of any one of the solid state forms of Rivoceranib and Rivoceranib mesylate of the present disclosure, or at least one of the above pharmaceutical compositions or formulations for the manufacture of medicaments for treating cancer.

BRIEF DESCRIPTION OF THE DRAWINGS

FIG. 11 shows a solid state $^{13}$C NMR spectrum of Form RT2 of Rivoceranib mesylate (range 100-200 ppm).

DETAILED DESCRIPTION OF THE DISCLOSURE

Figure 1:
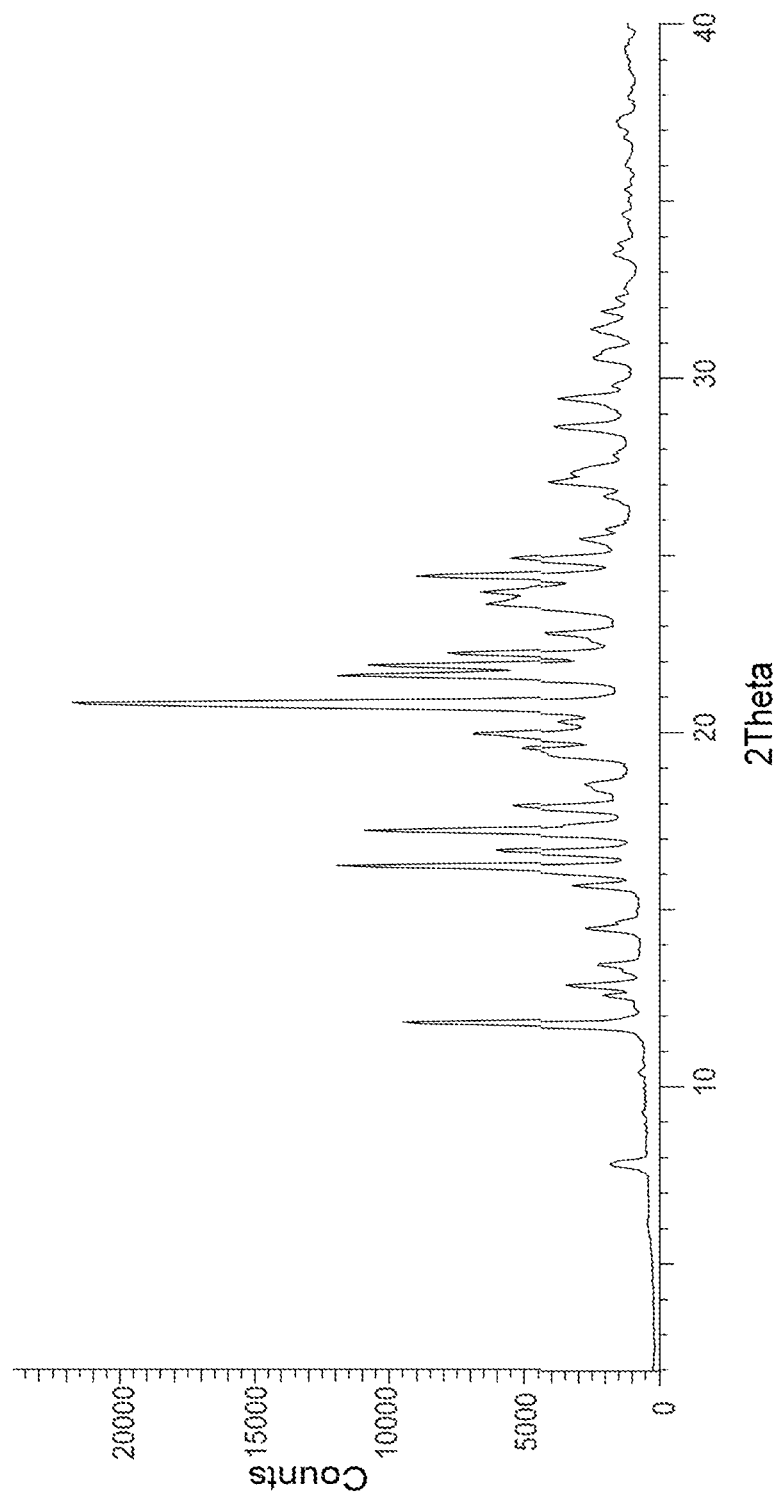
FIG. 1 shows a characteristic X-ray powder diffraction pattern (XRPD) of Rivoceranib Form RT1.

The present disclosure encompasses crystalline polymorphs of Rivoceranib and Rivoceranib mesylate, processes for preparation thereof, and pharmaceutical compositions including at least one of, or a combination of, these solid state forms. The disclosure also relates to the conversion of Rivoceranib and Rivoceranib mesylate and its solid state forms to other solid state forms of Rivoceranib, Rivoceranib mesylate and other salts of Rivoceranib.

The Rivoceranib and Rivoceranib mesylate and solid state forms thereof according to the present disclosure may have advantageous properties selected from at least one of the following: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Rivoceranib and Rivoceranib mesylate referred to herein as being characterized by graphical data "as depicted in" or "as substantially depicted in" a Figure will thus be understood to include any crystal forms of Rivoceranib and Rivoceranib mesylate characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state Forms RT1, RT2, RT3, RT4 and RT5 contain about 20% (w/w) or less, about 10% (w/w) or less, about 5% (w/w) or less, about 2% (w/w) or less, about 1% (w/w) or less, about 0.5% or less, or about 0% of any other forms of the subject compound as measured, for example, by XRPD. Thus, solid state Forms RT2, RT4 and RT5 of Rivoceranib mesylate and solid state Forms RT1 and RT3 of Rivoceranib described herein as substantially free of any other solid state forms would be understood to contain greater than about 80% (w/w), greater than about 90% (w/w), greater than about 95% (w/w), greater than about 98% (w/w), greater than about 99% (w/w), greater than about 99.5%, or about 100% of the subject crystalline polymorph of Rivoceranib mesylate and Rivoceranib, respectively.

In some embodiments of the disclosure, the described crystalline polymorphs of Rivoceranib mesylate and Rivoceranib may contain from about 0.5% to about 20% (w/w), from about 5% to about 20% (w/w), or from about 5% to about 10% (w/w) of one or more other solid state forms of Rivoceranib mesylate and Rivoceranib, respectively.

As used herein, unless stated otherwise, reference to % values are to wt %. This is based on the assumption that the solvent % in the various forms is measured in wt %.

As used herein, and unless stated otherwise, the term "anhydrous" in relation to crystalline forms of Rivoceranib and Rivoceranib mesylate, relates to a crystalline form of Rivoceranib and Rivoceranib mesylate which does not include any crystalline water (or other solvents) in a defined, stoichiometric amount within the crystal. Moreover, an "anhydrous" form would typically not contain more than 1% (w/w), of either water or organic solvents as measured for example by TGA (Thermal Gravimetric Analysis) or by using any other suitable method.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount. Stoichiometric amounts of two water molecules within the crystal structure is defined as a "dihydrate".

As used herein, the term "isolated" in reference to crystalline polymorph of Rivoceranib and Rivoceranib mesylate of the present disclosure corresponds to a crystalline polymorph of Rivoceranib and Rivoceranib mesylate that is physically separated from the reaction mixture in which it is formed.

As used herein, the term "stable" in relation to crystalline Rivoceranib and Rivoceranib mesylate refers to less than 20%, less than 10%, less than 5%, less than 2%, less than 1%, or less than 0.5% conversion of crystalline Rivoceranib or Rivoceranib mesylate to any other solid state form of Rivoceranib or Rivoceranib mesylate, respectively.

As used herein, unless stated otherwise, the XRPD measurements are taken using copper Kα radiation wavelength 1.54060 Å at a temperature of 25±3° C.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent.

In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

Figure 3:
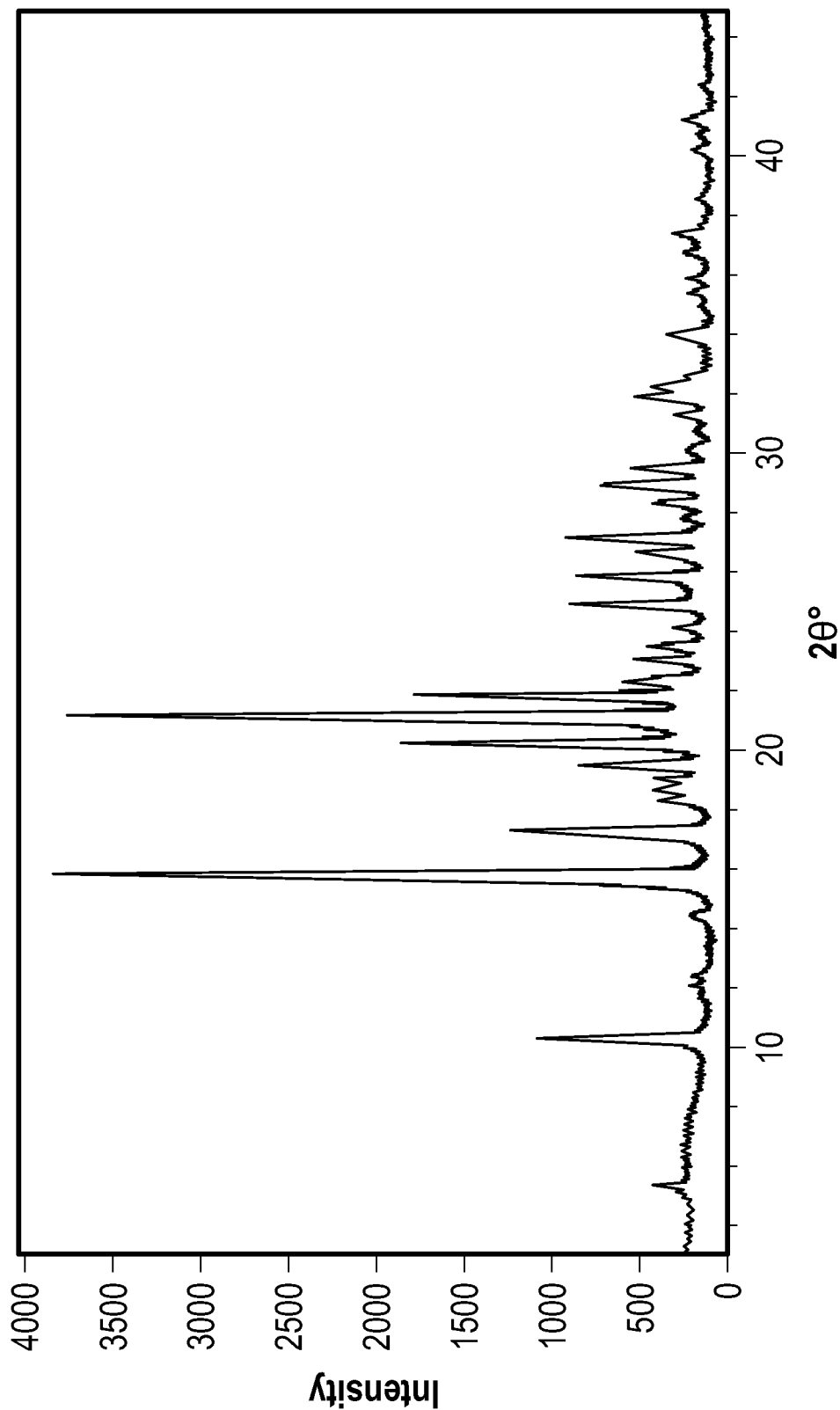
FIG. 3 shows a characteristic X-ray powder diffraction pattern (XRPD) of Rivoceranib mesylate Form A, as disclosed in U.S. Pat. No. 9,988,355 (FIG. 1).

As used herein the term "Form A" of Rivoceranib mesylate relates to a crystalline form having an XRPD shown herein in FIG. 3, or having characteristic XRPD 2-theta values at: 5.34, 10.341, 14.438, 15.841, 17.32, 18.301, 18.68, 19.005, 19.577, 20.26, 21.161, 21.859, 22.379, 23.04, 23.5, 24.177, 24.959, 25.881, 26.641, 27.18, 28.3, 28.999, 29.501, 1.96, 32.258, 33.999, 36.798, 37.38 and 41.297±0.2 degrees 2-theta, or as disclosed in in FIG. 1 of U.S. Pat. No. 9,988,355.

Figure 4:
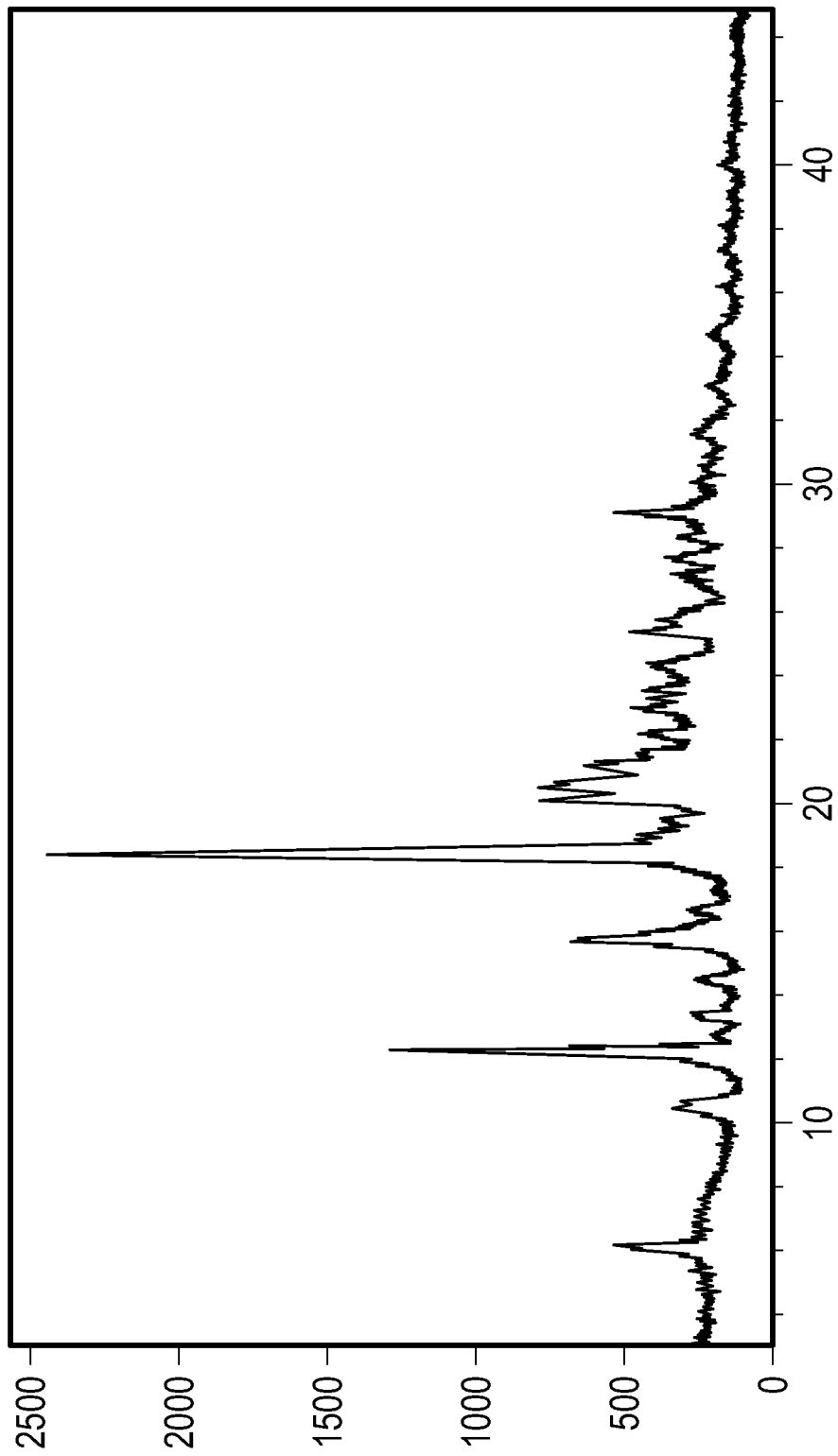
FIG. 4 shows a characteristic X-ray powder diffraction pattern (XRPD) of Rivoceranib Form D, as disclosed in patent publication CN104072410 (FIG. 1).

As used herein the term "Form D" of Rivoceranib relates to a crystalline form having an XRPD shown here in FIG. 4, or having characteristic XRPD 2-theta values at: 6.16, 10.441, 12.241, 12.774, 13.342, 14.498, 15.7, 16.66, 18.441, 19.463, 20.179, 20.559, 21.198, 22.219, 23, 23.558, 24.419, 25.4, 25.858, 27.219, 27.738, 28.354, 29.161 and 31.58±0.2 degrees 2-theta, or as disclosed in FIG. 1 of CN104072410. Rivoceranib mesylate Form D may be prepared according to CN104072410, or may be prepared according to the procedure described below (Example 1).

Figure 7:
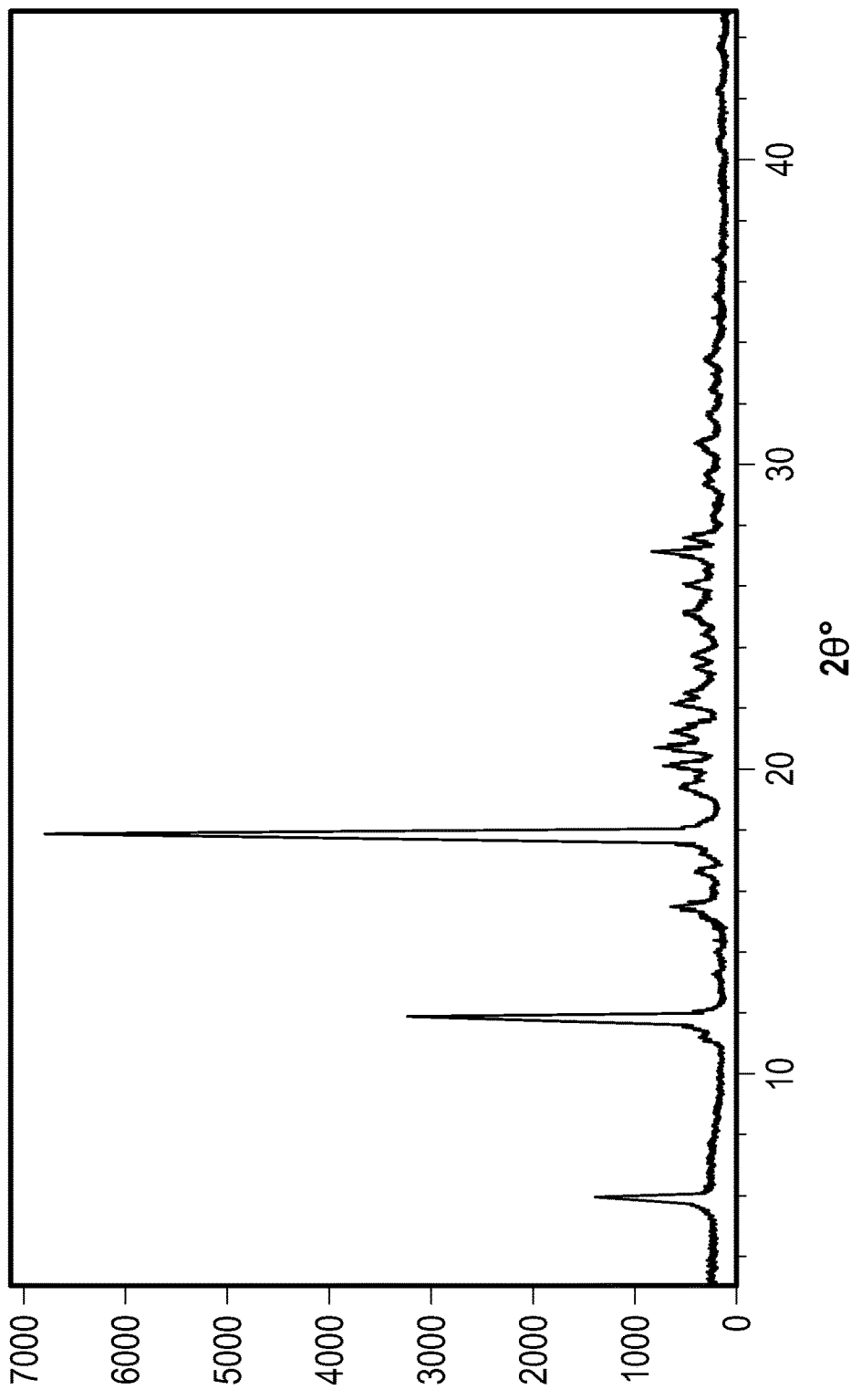
FIG. 7 shows a characteristic X-ray powder diffraction pattern (XRPD) of Rivoceranib Form B, as disclosed in CN105017142 (FIG. 1).

As used herein the term "Form B" of Rivoceranib relates to crystalline form having an XRPD shown here in FIG. 7, or having characteristic XRPD 2-theta values at: 5.919, 11.88, 15.537, 16.603, 17.899, 19.44, 20.16, 20.719, 21.241, 22.2, 22.54, 23.401, 23.779, 25.141, 26.119, 27.198 and 27.642±0.2 degrees 2-theta, as disclosed in FIG. 1 of CN105017142. Rivoceranib mesylate Form B may be prepared according to CN105017142, or may be prepared according to the procedure described below (Example 4).

The present disclosure includes a crystalline polymorph of Rivoceranib, designated Form RT1. The crystalline Form RT1 of Rivoceranib may be characterized by data selected from one or more of the following: an X-ray powder diffraction pattern substantially as depicted in FIG. 1; an X-ray powder diffraction pattern having peaks at 11.6, 16.4, 17.0, 17.7 and 20.5 degrees 2-theta±0.2 degrees 2-theta; and combinations of these data.

Crystalline Form RT1 of Rivoceranib may be further characterized by an X-ray powder diffraction pattern having peaks at 11.6, 16.4, 17.0, 17.7 and 20.5 degrees 2-theta±0.2 degrees 2-theta, and also having any one, two, three, four or five additional peaks selected from 7.6, 16.0, 19.7, 24.2 and 24.7 degrees 2-theta±0.2 degrees 2-theta.

Crystalline Form RT1 of Rivoceranib may alternatively be characterized by an XRPD pattern having peaks at 7.6, 11.6, 16.0, 16.4, 17.0, 17.7, 19.7, 20.5, 24.2 and 24.7 degrees 2-theta±0.2 degrees 2-theta.

In another embodiment crystalline Rivoceranib Form RT1 may be characterized as anhydrous form.

Crystalline Form RT1 of Rivoceranib may be characterized by each of the above characteristics alone or by all possible combinations, e.g., an XRPD pattern having peaks at 11.6, 16.4, 17.0, 17.7 and 20.5 degrees 2-theta±0.2 degrees 2-theta; an XRPD pattern as depicted in FIG. 1, and combinations thereof.

In another embodiment of the present disclosure, Rivoceranib Form RT1 is polymorphically pure.

In one embodiment of the present disclosure, crystalline Form RT1 of Rivoceranib is isolated.

As discussed above, depending on which other solid state it is compared with, Form RT1 of Rivoceranib according to the present disclosure may have advantageous properties as described above.

Figure 2:
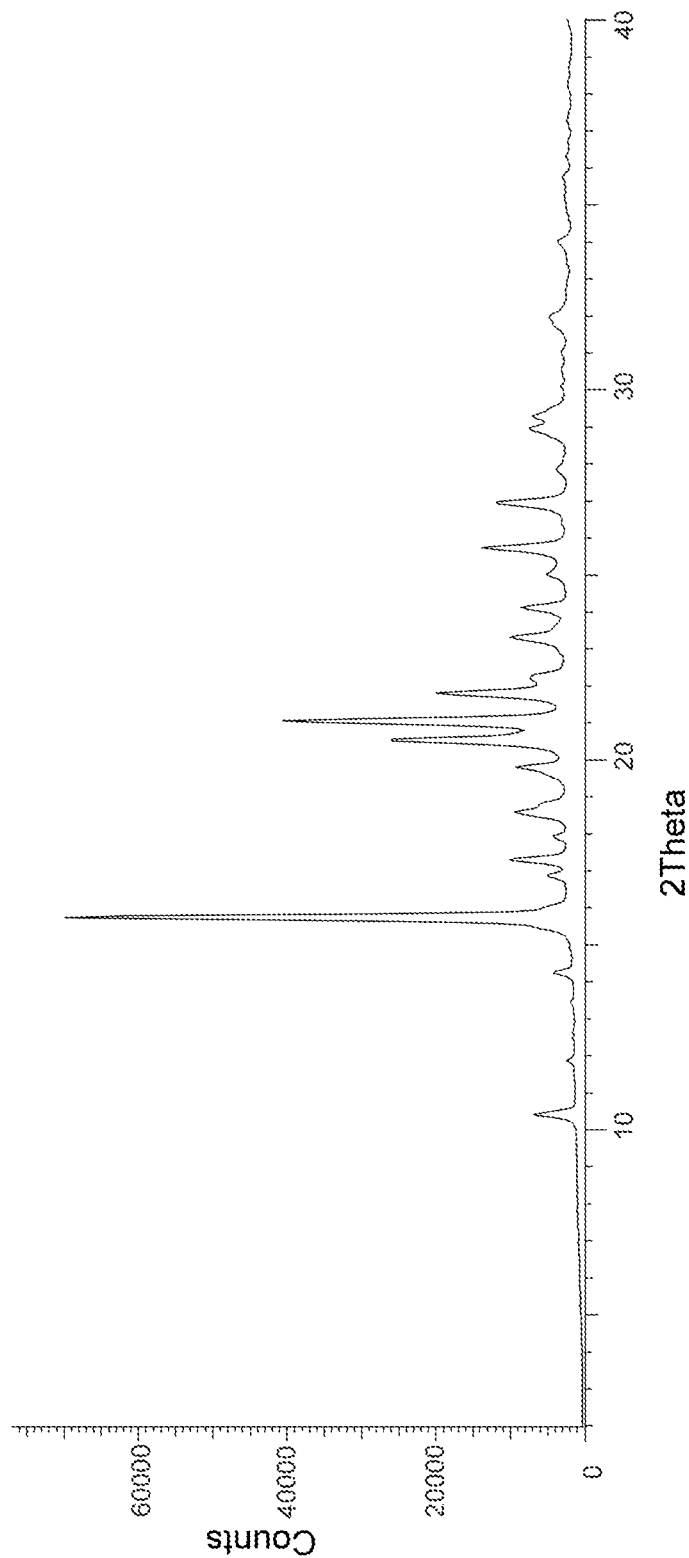
FIG. 2 shows a characteristic X-ray powder diffraction pattern (XRPD) of Rivoceranib mesylate Form RT2.

The present disclosure further includes a crystalline polymorph of Rivoceranib mesylate, designated Form RT2. The crystalline Form RT2 of Rivoceranib mesylate may be characterized by data selected from one or more of the following: an X-ray powder diffraction pattern substantially as depicted in FIG. 2; an X-ray powder diffraction pattern having peaks at 10.4, 11.9, 14.2, 19.8, 20.5 and 27.0 degrees 2-theta±0.2 degrees 2-theta and having absence of peaks at 18.3, 19.6, 23.0 and 26.6 degrees 2-theta±0.2 degrees 2-theta; an X-ray powder diffraction pattern having peaks at 10.4, 14.2, 16.8, 17.9, 19.8, 20.5 and 23.3 degrees 2-theta±0.2 degrees 2-theta and having absence of peaks at 5.3, 19.0, 19.6, 23.0, 26.6 and 28.3 degrees 2-theta±0.2 degrees 2-theta; and combinations of these data.

Crystalline Form RT2 of Rivoceranib mesylate may be further characterized by an X-ray powder diffraction pattern having peaks at 10.4, 11.9, 14.2, 19.8, 20.5 and 27.0 degrees 2-theta±0.2 degrees 2-theta and having absence of peaks at 18.3, 19.6, 23.0 and 26.6 degrees 2-theta±0.2 degrees 2-theta, and also having any one, two, three, four or five additional peaks selected from 15.8, 16.8, 21.8, 24.1 and 25.7 degrees 2-theta±0.2 degrees 2-theta.

Crystalline Form RT2 of Rivoceranib mesylate may alternatively be characterized by an XRPD pattern having peaks at 10.4, 11.9, 14.2, 15.8, 16.8, 19.8, 20.5, 21.8, 24.1, 25.7 and 27.0 degrees 2-theta±0.2 degrees 2-theta and having absence of peaks at 18.3, 19.6, 23.0 and 26.6 degrees 2-theta±0.2 degrees 2-theta.

In another embodiment of the present disclosure, crystalline Rivoceranib mesylate Form RT2 may be characterized as a hydrate.

Crystalline Rivoceranib mesylate RT2 may possess water content of from about 5 to about 8%, in embodiments about 6.4%, as measured by Karl Fischer. Accordingly, form RT2 may be a hydrate, in embodiments a dihydrate.

Figure 9:
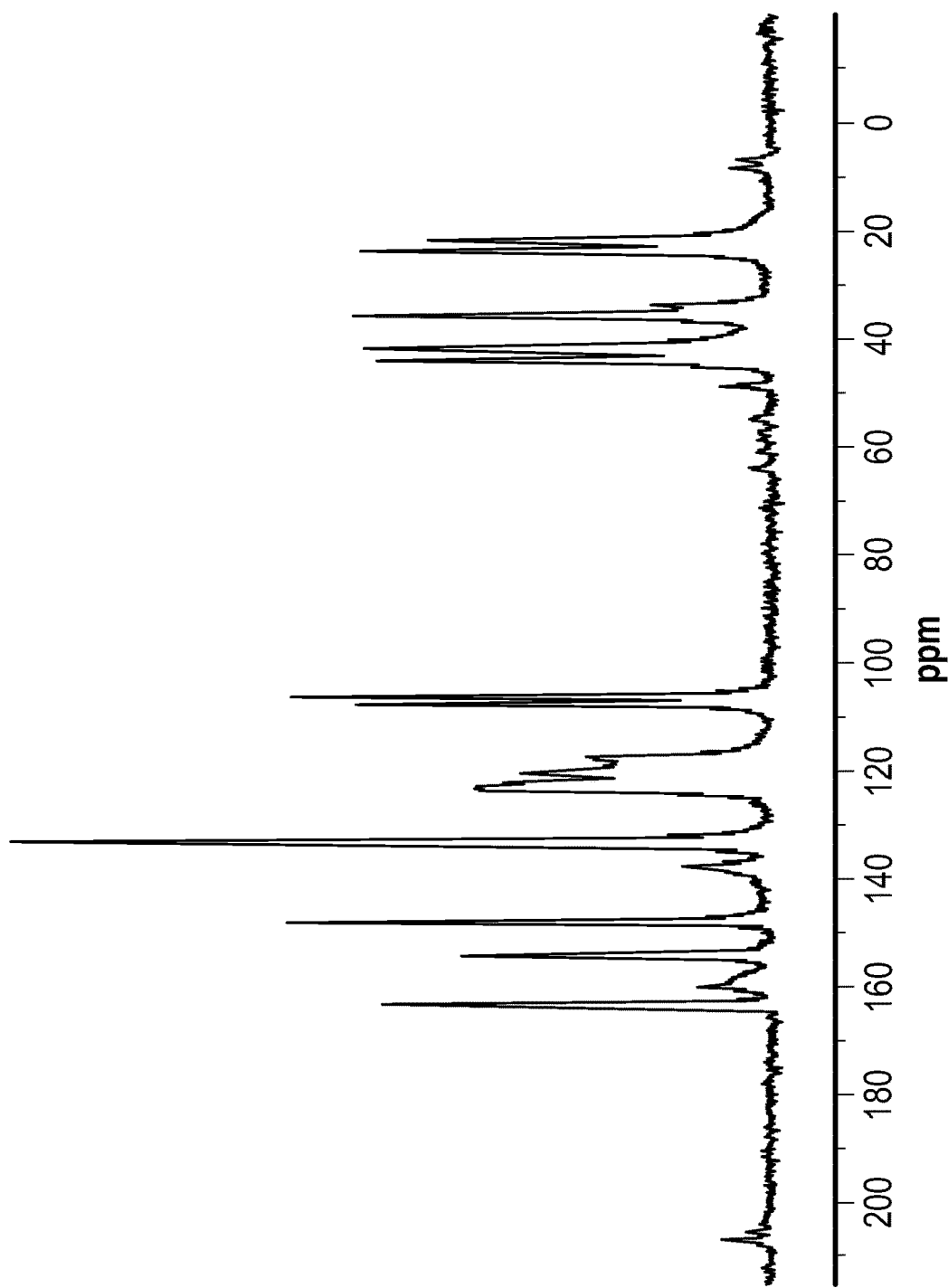
FIG. 9 shows a solid state $^{13}$C NMR spectrum of Form RT2 of Rivoceranib mesylate (full range 0-200 ppm).
Figure 10:
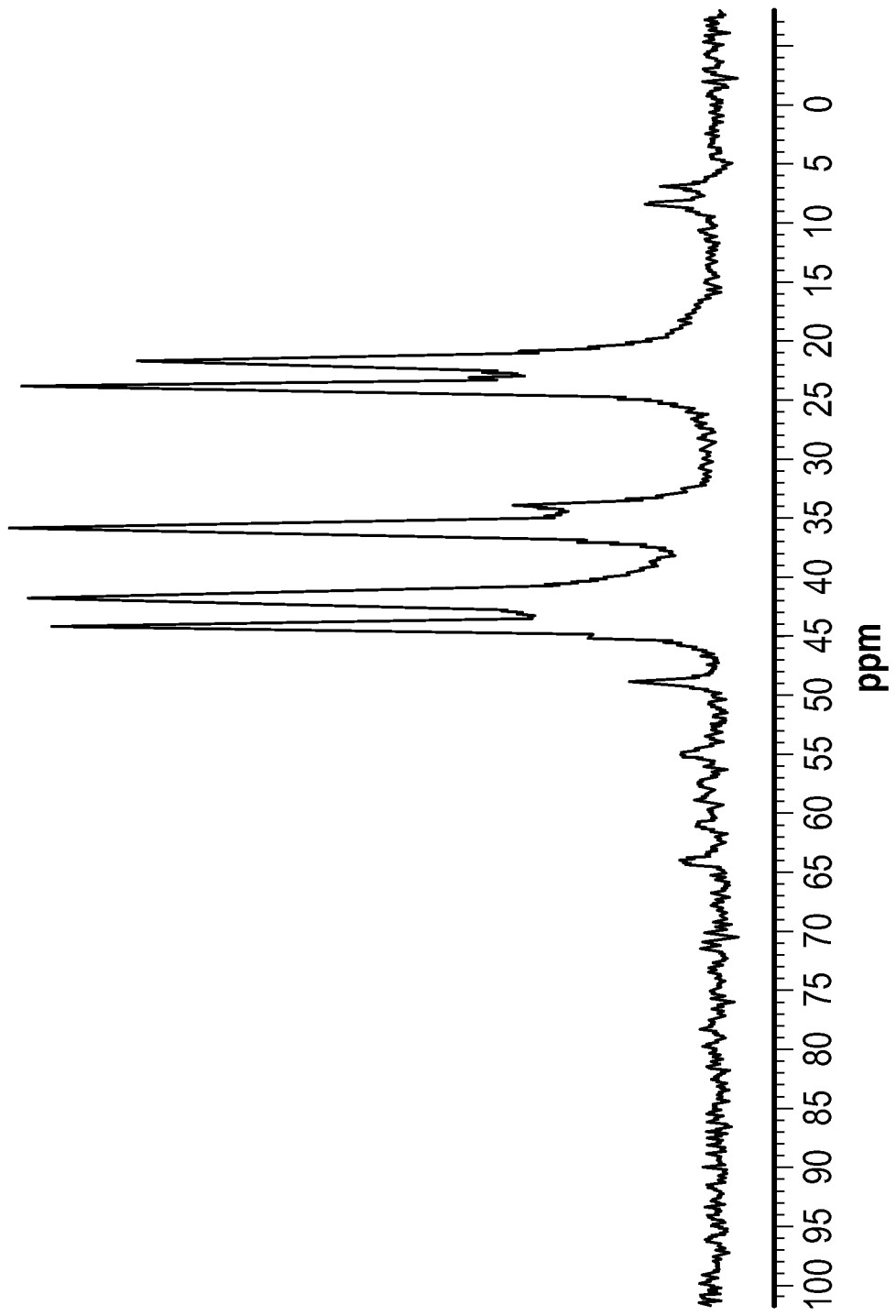
FIG. 10 shows a solid state $^{13}$C NMR spectrum of Form RT2 of Rivoceranib mesylate (range 0-100 ppm).

In some embodiments, crystalline form RT2 of Rivoceranib mesylate may be characterized by a solid state $^{13}C$ NMR spectrum having peaks at 21.7, 23.7, 33.9, 35.8, 44.2 and 133.3 ppm±0.2 ppm; a solid state $^{13}C$ NMR spectrum having the following chemical shift absolute differences from a reference peak at 48.6 ppm±2 ppm of 26.9, 24.9, 14.7, 12.8, 4.4 and 84.7 ppm±0.1 ppm; and/or a solid state $^{13}C$ NMR spectrum substantially as depicted in FIG. 9, 10 or 11.

Crystalline Form RT2 of Rivoceranib mesylate may be characterized by each of the above characteristics alone/or by all possible combinations, e.g., an XRPD pattern having peaks at 10.4, 11.9, 14.2, 19.8, 20.5 and 27.0 degrees 2-theta±0.2 degrees 2-theta and having absence of peaks at 18.3, 19.6, 23.0 and 26.6 degrees 2-theta±0.2 degrees; an XRPD pattern having peaks at 10.4, 14.2, 16.8, 17.9, 19.8, 20.5 and 23.3 degrees 2-theta±0.2 degrees 2-theta and having absence of peaks at 5.3, 19.0, 19.6, 23.0, 26.6 and 28.3 degrees 2-theta±0.2 degrees 2-theta; an XRPD pattern as depicted in FIG. 2, and combinations thereof.

In another embodiment of the present disclosure, Rivoceranib mesylate Form RT2 is polymorphically pure.

In one embodiment of the present disclosure, crystalline Form RT2 of Rivoceranib mesylate is isolated.

As discussed above, depending on which other solid state it is compared with, Form RT2 of Rivoceranib according to the present disclosure may have advantageous properties as described above. Particularly, crystalline Form RT2 of Rivoceranib mesylate of the present disclosure is stable, for example upon exposure to high humidity or high temperature or high mass pressure conditions, such as 60° C./100% RH for up to 7 days or 80% RH at room temperature for 2 days, or under 100° C. for 60 minutes or under mass pressure of 2 ton for 1 minute.

A process for preparing Crystalline Form RT2 Rivoceranib mesylate includes slurrying Rivoceranib mesylate, in embodiments Rivoceranib mesylate form A, in a mixture including water, and drying.

The process includes, in embodiments:

a) mixing Rivoceranib mesylate, in embodiments Rivoceranib mesylate form A, water and optionally a solvent selected from: 2-ethoxyethanol, ethanol, toluene, or combinations thereof, to obtain a slurry, and optionally stirring;

b) separating the solid from the mixture, in embodiments by filtration; and c) optionally drying the solid.

In one embodiment, the mixture in step (a) optionally includes a solvent selected from one of: 2-ethoxyethanol, ethanol, or toluene.

In another embodiment, the 2-ethoxyethanol, ethanol, toluene, or combinations thereof, is present in a volume ratio to water of about 1:5 to about 1:50, about 1:10 to about 1:25, about 1:10 to about 1:20, and in embodiments about 1:15.

In another embodiment, the mixture in step (a) includes water in an amount of: about 2 ml to about 50 ml, about 5 ml to about 40 ml, about 8 ml to about 30 ml, about 8 ml to about 25 ml, per gram of Rivoceranib mesylate.

In any embodiment of the process for preparing Rivoceranib mesylate form RT2, the mixture in step (a) is stirred. The stirring may carried out for a sufficient time to enable the preparation of Form RT2 of Rivoceranib mesylate. In aspects the mixture in step (a) is stirred for: about 4 hours to about 128 hours, about 4 hours to about 96 hours, about 5 hours to about 80 hours, in embodiments about 12 to about 80 hours.

In any embodiment of the process for preparing Rivoceranib mesylate form RT2, the mixture in step (a) is stirred at a temperature of about 15° C. to about 80° C., about 18° C. to about 70° C., about 20° C. to about 65° C., or about 18 to about 30° C.

In one embodiment of the process for preparing Rivoceranib mesylate form RT2, the mixture in step (a) is stirred at about 50° C. to about 80° C., in embodiments for about 4 to about 10 hours, or about 60° C., for about 6 hours. In an aspect, the mixture in step (a) is a mixture of the Rivoceranib mesylate and water.

In another embodiment of the process for preparing Rivoceranib mesylate form RT2, the mixture in step (a) is stirred at about 15° C. to about 50° C., in embodiments for about 12 to about 90 hours, or about 18° C. to about 35° C., in embodiments for about 20 to about 75 hours, or about 20° C. to about 30° C., in embodiments for about 24 to about 72 hours. In an aspect, the mixture in step (a) is a mixture of the Rivoceranib mesylate and water.

In another embodiment of the process for preparing Rivoceranib mesylate form RT2, the mixture in step (a) is filtered, in embodiments at a temperature of about 15° C. to about 40° C., about 18° C. to about 35° C., in embodiments about 20° C. to about 30° C. The solid may be dried on the filter under suction, in embodiments for about 2 to about 80 minutes, about 5 to about 70 minutes, about 10 to about 60 minutes, or about 10 to about 30 minutes.

In another embodiment of the process for preparing Rivoceranib mesylate form RT2, the solid is further dried at about 15° C. to about 35° C., about 20° C. to about 35° C., or about 25 to 35° C. In embodiments the drying is for about 8 to about 72 hours, about 12 to about 50 hours, or about 24 to about 40 hours.

The processes as described herein may further include combining the Rivoceranib mesylate with at least one pharmaceutically acceptable excipient to form a pharmaceutical composition.

The present disclosure further includes a crystalline polymorph of Rivoceranib, designated Form RT3. The crystalline Form RT3 of Rivoceranib may be characterized by data selected from one or more of the following: an X-ray powder diffraction pattern substantially as depicted in FIG. 5; an X-ray powder diffraction pattern having peaks at 16.0, 17.1, 18.2, 20.0 and 20.5 degrees 2-theta±0.2 degrees 2-theta; and combinations of these data.

Crystalline Form RT3 of Rivoceranib may be further characterized by an X-ray powder diffraction pattern having peaks at 16.0, 17.1, 18.2, 20.0 and 20.5 degrees 2-theta±0.2 degrees 2-theta, and also having any one, two, three, four or five additional peaks selected from 6.0, 12.1, 19.2, 23.0 and 24.2 degrees 2-theta±0.2 degrees 2-theta.

Crystalline Form RT3 of Rivoceranib may alternatively be characterized by an XRPD pattern having peaks at 6.0, 12.1, 16.0, 17.1, 18.2, 19.2, 20.0, 20.5, 23.0 and 24.4 degrees 2-theta±0.2 degrees 2-theta.

Figure 5:
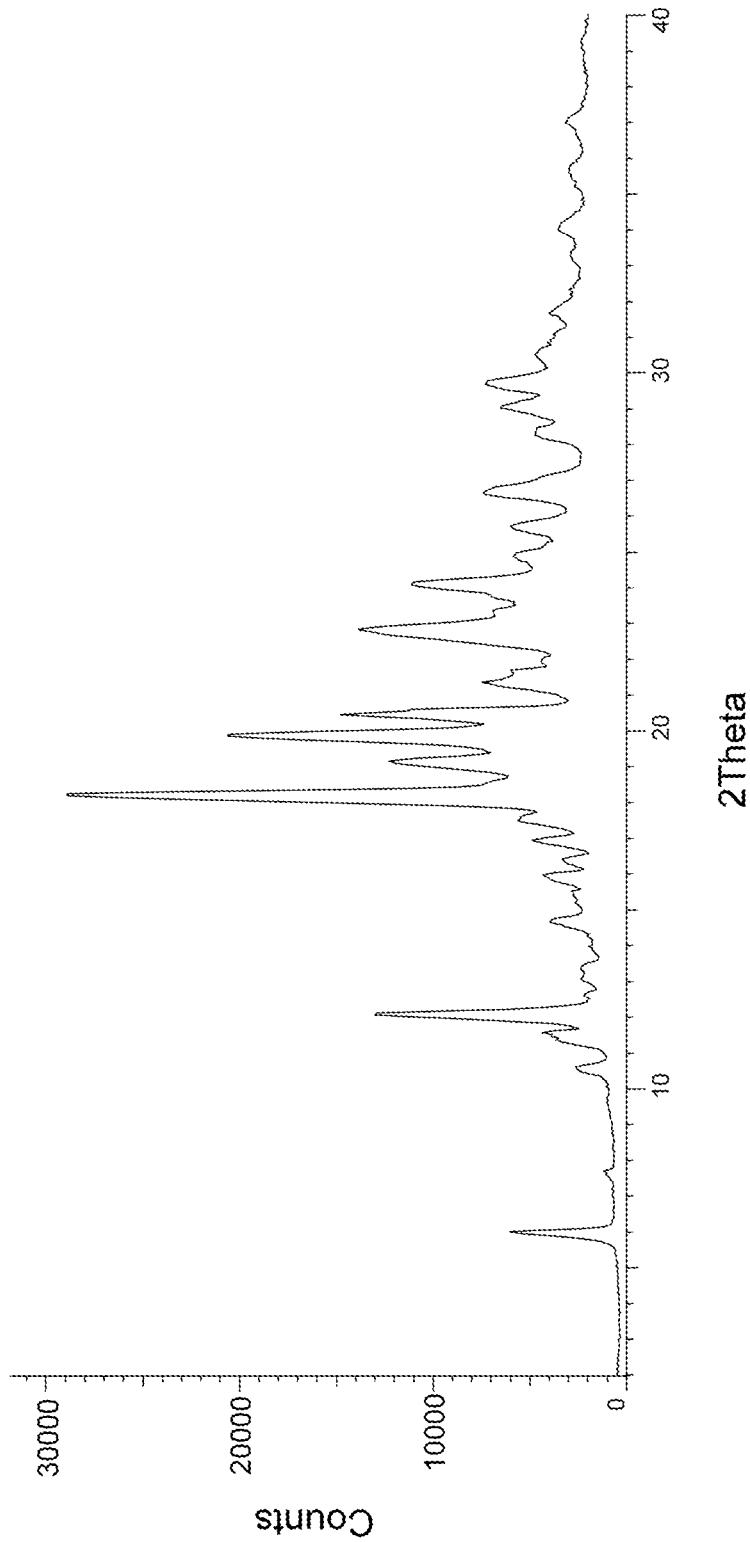
FIG. 5 shows a characteristic X-ray powder diffraction pattern (XRPD) of Rivoceranib Form RT3.

Crystalline Form RT3 of Rivoceranib may be characterized by each of the above characteristics alone or by all possible combinations, e.g., an XRPD pattern having peaks at 16.0, 17.1, 18.2, 20.0 and 20.5 degrees 2-theta±0.2 degrees 2-theta; an XRPD pattern as depicted in FIG. 5, and combinations thereof.

In another embodiment of the present disclosure, crystalline Rivoceranib Form RT3 may be characterized as a hydrate, such as hemihydrate.

In another embodiment of the present disclosure, Rivoceranib Form RT3 is polymorphically pure.

In one embodiment of the present disclosure, crystalline Form RT3 of Rivoceranib is isolated.

The present disclosure further comprises a crystalline polymorph of Rivoceranib mesylate, designated Form RT4. The crystalline Form RT4 of Rivoceranib mesylate may be characterized by data selected from one or more of the following: an X-ray powder diffraction pattern substantially as depicted in FIG. 6; an X-ray powder diffraction pattern having peaks at 14.8, 17.0, 20.1, 21.7 and 26.6 degrees 2-theta±0.2 degrees 2-theta; and combinations of these data.

Crystalline Form RT4 of Rivoceranib mesylate may be further characterized by an X-ray powder diffraction pattern having peaks at 14.8, 17.0, 20.1, 21.7 and 26.6 degrees 2-theta±0.2 degrees 2-theta, and also having any one, two, three, four or five additional peaks selected from 17.5, 18.4, 19.1, 22.3 and 26.0 degrees 2-theta±0.2 degrees 2-theta.

Crystalline Form RT4 of Rivoceranib mesylate may alternatively be characterized by an XRPD pattern having peaks at 14.8, 17.0, 17.5, 18.4, 19.1, 20.1, 21.7, 22.3, 26.0 and 26.6 degrees 2-theta±0.2 degrees 2-theta.

Figure 6:
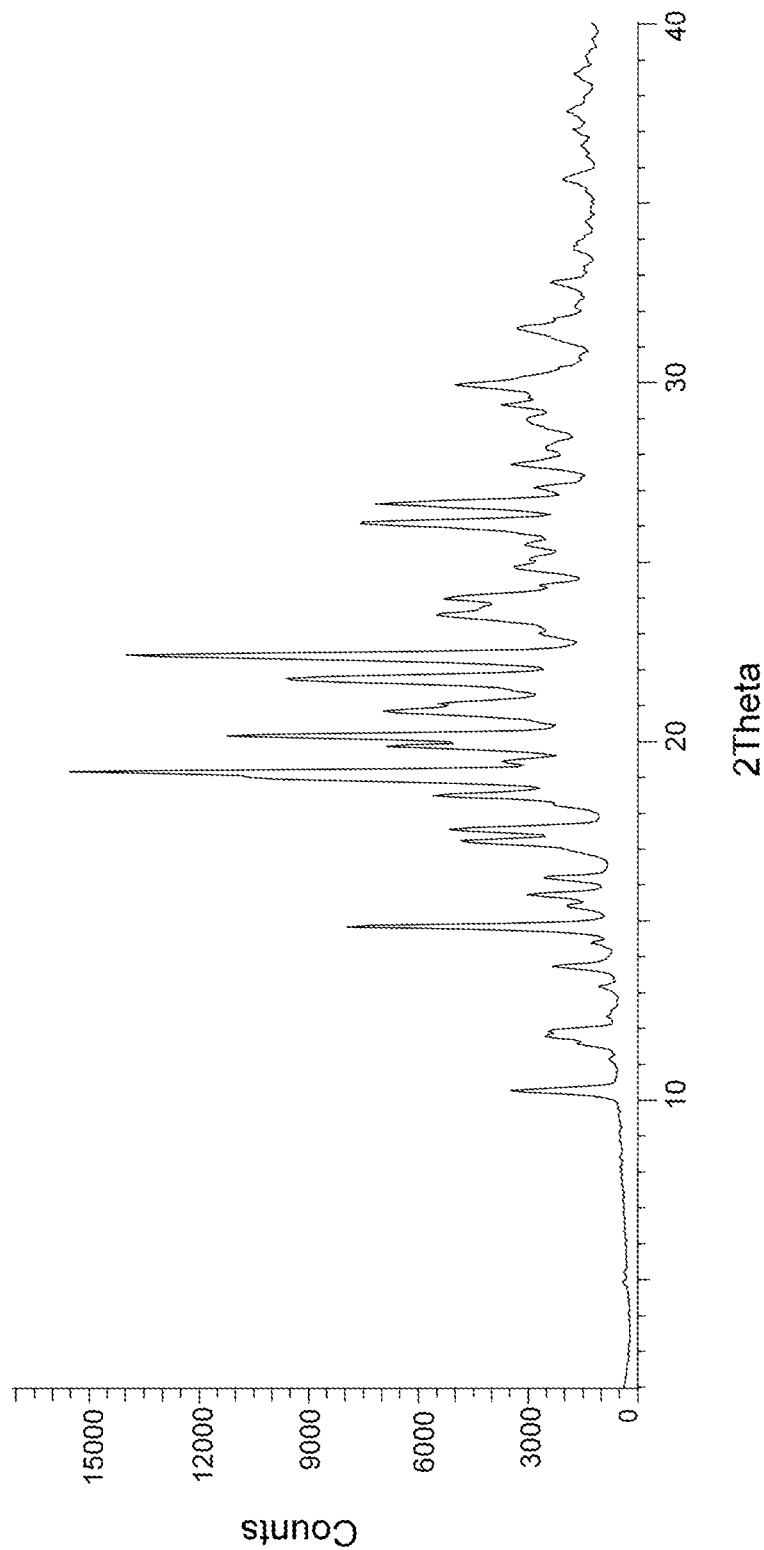
FIG. 6 shows a characteristic X-ray powder diffraction pattern (XRPD) of Rivoceranib mesylate Form RT4.

Crystalline Form RT4 of Rivoceranib mesylate may be characterized by each of the above characteristics alone or by all possible combinations, e.g., an XRPD pattern having peaks at 14.8, 17.0, 20.1, 21.7 and 26.6 degrees 2-theta±0.2 degrees 2-theta; an XRPD pattern as depicted in FIG. 6, and combinations thereof.

In another embodiment of the present disclosure, crystalline Rivoceranib mesylate Form RT4 may be characterized as a hydrate.

In another embodiment of the present disclosure, Rivoceranib mesylate Form RT4 is polymorphically pure.

In one embodiment of the present disclosure, crystalline Form RT4 of Rivoceranib mesylate is isolated.

The present disclosure comprises a crystalline polymorph of Rivoceranib mesylate, designated Form RT5. The crystalline Form RT5 of Rivoceranib mesylate may be characterized by data selected from one or more of the following: an X-ray powder diffraction pattern substantially as depicted in FIG. 8; an X-ray powder diffraction pattern having peaks at 10.1, 13.9, 16.2, 18.6, 20.0 and 26.0 degrees 2-theta±0.2 degrees 2-theta; and combinations of these data.

Crystalline Form RT5 of Rivoceranib mesylate may be further characterized by an X-ray powder diffraction pattern having peaks at 10.1, 13.9, 16.2, 18.6, 20.0 and 26.0 degrees 2-theta±0.2 degrees 2-theta, and also having any one, two, three or four additional peaks selected from 4.5, 10.6, 15.6 and 27.8 degrees 2-theta±0.2 degrees 2-theta.

Crystalline Form RT5 of Rivoceranib mesylate may alternatively be characterized by an XRPD pattern having peaks at 4.5, 10.1, 10.6, 13.9, 15.6, 16.2, 18.6, 20.0, 26.0 and 27.8 degrees 2-theta±0.2 degrees 2-theta.

Figure 8:
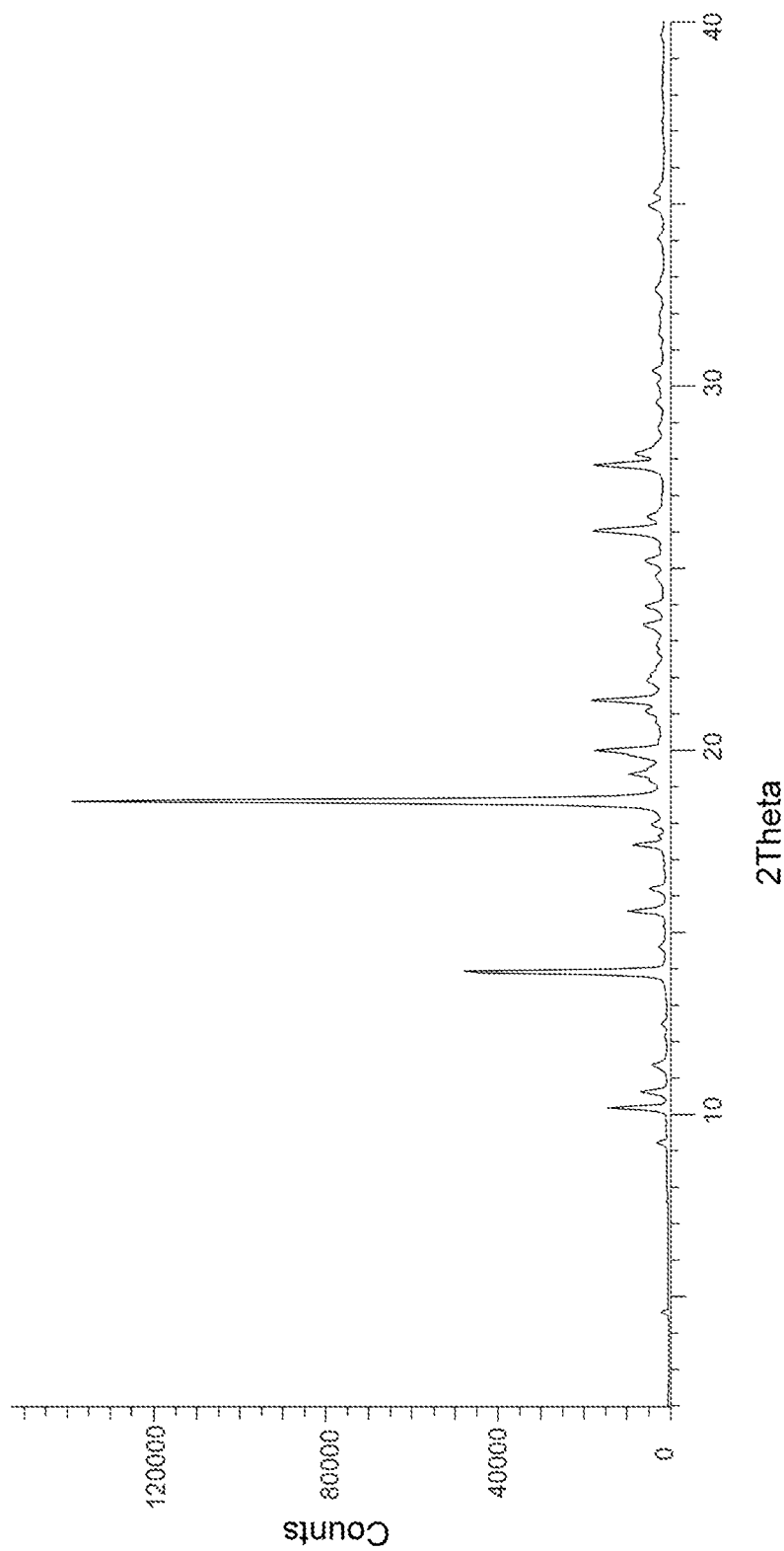
FIG. 8 shows a characteristics X-ray powder diffraction pattern (XRPD) of Rivoceranib mesylate Form RT5.

Crystalline Form RT5 of Rivoceranib mesylate may be characterized by each of the above characteristics alone or by all possible combinations, e.g., an XRPD pattern having peaks at 10.1, 13.9, 16.2, 18.6, 20.0 and 26.0 degrees 2-theta±0.2 degrees 2-theta; an XRPD pattern as depicted in FIG. 8, and combinations thereof.

In another embodiment Crystalline Rivoceranib mesylate Form RT5 may be characterized as an acetic acid solvate.

In another embodiment of the present disclosure, Rivoceranib mesylate Form RT5 is polymorphically pure.

In one embodiment of the present disclosure, crystalline Form RT5 of Rivoceranib mesylate is isolated.

The above processes can further include a step of combining Rivoceranib or Rivoceranib mesylate crystalline form with at least one pharmaceutically acceptable excipient to prepare a pharmaceutical composition or a pharmaceutical formulation.

The present disclosure also relates to the use of any one or a combination of the described crystalline polymorphs of Rivoceranib and Rivoceranib mesylate, for preparing other crystalline polymorphs of Rivoceranib, Rivoceranib mesylate or other rivoceranib salts and their solid state forms thereof.

The present disclosure also relates to any one or a combination of the described crystalline polymorphs of Rivoceranib and Rivoceranib mesylate of the present disclosure, for use in the preparation of other crystalline polymorphs of Rivoceranib, Rivoceranib mesylate or other Rivoceranib salts and their solid state forms thereof.

In another aspect, the present disclosure encompasses any one or combination of the above described crystalline polymorphs of Rivoceranib and Rivoceranib mesylate for use in the preparation of pharmaceutical compositions and/or formulations for use in medicine, in embodiments for the treatment of cancer.

In another embodiment, the present disclosure also encompasses the uses of any one or combinations of the above described crystalline polymorphs of Rivoceranib and Rivoceranib mesylate for the preparation of pharmaceutical compositions and/or formulations, for use in medicine, in embodiments for the treatment of cancer.

The present disclosure includes processes for preparing the above mentioned pharmaceutical compositions. The processes include combining any one or combination of the crystalline polymorphs of Rivoceranib and/or Rivoceranib mesylate of the present disclosure with at least one pharmaceutically acceptable excipient.

Pharmaceutical formulations of the present disclosure contain any one or a combination of the crystalline polymorphs of Rivoceranib and Rivoceranib mesylate of the present disclosure, in embodiments crystalline Rivoceranib mesylate Forms RT2, RT4 and RT5 and crystalline Rivoceranib Forms RT1 and RT3. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present disclosure, Rivoceranib and/or Rivoceranib mesylate and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum, and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, in embodiments a powdered or granulated solid composition of the disclosure, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, which causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Rivoceranib and Rivoceranib mesylate can be administered to mammals. Rivoceranib and Rivoceranib mesylate may be formulated for administration to a mammal, in embodiments a human, by injection. Rivoceranib and Rivoceranib mesylate can be formulated, for example, as a viscous liquid solution or suspension, in embodiments a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorphs of Rivoceranib and of Rivoceranib mesylate and the pharmaceutical compositions of Rivoceranib and of Rivoceranib mesylate of the present disclosure can be used as medicaments, in embodiments in the treatment of cancer.

In another embodiment, Rivoceranib mesylate Forms RT2, RT4 and RT5 and Rivoceranib Forms RT1 and RT3 and the pharmaceutical compositions of Rivoceranib mesylate Forms RT2, RT4 and RT5 and Rivoceranib Forms RT1 and RT3 can be used as medicaments, in embodiments in the treatment of cancer.

The present disclosure also provides methods of treating cancer by administering a therapeutically effective amount of crystalline polymorphs of Rivoceranib and of Rivoceranib mesylate of the present disclosure, or at least one of the above pharmaceutical compositions and/or formulation, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

ANALYTICAL METHODS

Powder X-Ray Diffraction (XRD) Method

X-ray diffraction was performed on X-Ray powder diffractometer:
Bruker D8 Advance; CuK radiation ($\lambda$=1.5418 Å) Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.
Measurement parameters:
  Scan range: 2-40 degrees 2-theta;
  Scan mode: continuous;
  Step size: 0.05 degrees;
  Time per step: 0.5 s;
  Sample spin: 30 rpm;
  Sample holder: PMMA specimen holder ring.
Solid-state $^{13}$C NMR Method
  Solid-state $^{13}$C NMR spectra were recorded with variable amplitude cross polarization, magic angle spinning and high power proton decoupling using a BRUKER Avance III+ spectrometer operating at 400 MHZ at room temperature. A probe using 4 mm o.d. zirconia rotors was employed. The operation conditions were: contact time: 3 ms; recycle delay: 2 s; 5100 scans and spin rate of 11 KHz. Chemical shifts were referenced via a replacement sample of glycine (carboxyl carbon chemical shift assigned as 176.03 ppm relative to the signal of tetramethylsilane).

EXAMPLES

Rivoceranib Form D and Form B were used as the starting material for the preparation of form RT1 and Rivoceranib mesylate Form A was used as the starting material for the preparation of Form RT1-RT5. Rivoceranib mesylate Form A and Rivoceranib Form D can be prepared according to the procedure described in U.S. Pat. No. 9,988,355 and in CN104072410, respectively. Rivoceranib Form D can be also prepared according to Example 1 described below. Rivoceranib Form B can be prepared according to the procedure described in CN105017142 patent publication (examples 1-3) and also according to Example 4 described herein.

Example 1. Preparation of Form D

Rivoceranib mesylate (Form A) 2.0 grams was dissolved in 50 ml of methanol at 40° C. in 250 ml round bottom flask, filtered the clear solution under vacuum (particle free filtration). Transferred the clear solution into 2000 ml round bottom flask and added 1000 ml of water at 20-30° C. in 30-60 minutes, maintained for 4 hours at 20-30° C. and the obtained slurry was kept overnight at 20-30° C. The compound was filtered under vacuum at 20-30° C. and kept for drying under suction for about 10-30 minutes at 20-30° C. to obtain Form D (0.4 grams).

Example 2. Preparation of Rivoceranib Form RT1

Rivoceranib (Form D) 0.1 grams was dried at 110° C. for 2 hours in air tray dryer to obtain Form RT1. The obtained solid was analyzed by XRPD and confirmed Form RT1 (FIG. 1).

Example 3. Preparation Rivoceranib Mesylate Form RT2

Rivoceranib mesylate (Form A) 2 grams was taken into 250 ml round bottom flask and added in 20 ml of water at 20-30° C. The obtained slurry was stirred for 3 days at same temperature. The obtained solid was filtered under vacuum at 25-30° C. and kept under suction for about 30 minutes to get Form RT2 which was kept open under air dry for 38 hours at 25-30° C. for further drying. The obtained solid was analyzed by XRPD and confirmed Form RT2 (FIG. 2, 1.5 grams).

Example 4. Preparation Rivoceranib Form B

Rivoceranib mesylate (Form A) 3.0 grams was dissolved in 3.0 ml of methanol and 30 ml of water at 55° C. in 250 ml round bottom flask to obtain the clear solution. The clear solution was cooled to 25-30° C. in 60-120 minutes under stirring. The obtained slurry was maintained for 2 days at same temperature (25-30° C.), then cooled to 5° C. in 30-60 minutes and kept at this low temperature for additional 2 hours. The obtained solid was filtered under vacuum at 20-30° C. and kept for suction for about 10-30 minutes at 20-30° C. to obtain Form B (0.9 grams).

Example 5. Preparation of Rivoceranib Form RT1

Rivoceranib mesylate (Form A) 70 mg was placed in 5 ml vial, added in 0.1 ml of Isopropyl acetate and 1.5 ml water at 20-30° C. and the obtained slurry was stirred for 2 days at same temperature. The obtained solid was filtered under vacuum at 25-30° C. and kept under suction for about 10-20 minutes to obtain Form RT1.

Example 6. Preparation of Rivoceranib Form RT1

Rivoceranib mesylate (Form B) 0.1 grams was dried at 100° C. for 1 hour in air tray dryer to obtain Form RT1.

Example 7. Preparation Rivoceranib Mesylate Form RT2

Rivoceranib mesylate (Form A) 70 mg was placed in 5 ml vial, added in 0.1 ml of Toluene and 1.5 ml water at 20-30° C. and the obtained slurry was stirred for 1 day at same temperature. The obtained solid was filtered under vacuum at 25-30° C. and kept under suction for about 10-20 minutes to obtain Form RT2.

Example 8. Preparation Rivoceranib Mesylate Form RT2

Rivoceranib mesylate (Form A) 70 mg was placed in 5 ml vial, added in 0.1 ml of Ethanol and 1.5 ml water at 20-30° C. and the obtained slurry was stirred for 2 days at same temperature. The obtained solid was filtered under vacuum at 25-30° C. and kept under suction for about 10-20 minutes to obtain Form RT2.

Example 9. Preparation Rivoceranib Form RT3

Rivoceranib mesylate (Form A) 0.5 grams was placed in 250 ml round bottom flask and added in 100 ml of water at 20-30° C. and the obtained slurry was stirred for 2 days at same temperature. The obtained solid was filtered under vacuum at 25-30° C. and kept under suction for about 180 minutes under vacuum and was further kept open to air dry for 24 hours at 25-30° C. to obtain Form RT3 (0.3 grams).

Example 10. Preparation Rivoceranib Form RT3

Rivoceranib mesylate (Form A) 0.5 grams was placed in 250 ml round bottom flask and added in 20 ml of DMF(N, N-Dimethyl Formamide) at 20-30° C. and stirred for 5 minutes at same temperature to obtain a clear solution. To the clear solution was added 150 ml of water under stirring, the clear solution became cloudy and stirring was continued for 24 hours at same temperature. The obtained solid was filtered under vacuum at 25-30° C. and kept under suction for about 60 minutes to obtain Form RT3 (0.28 grams).

Example 11. Preparation Rivoceranib Mesylate Form RT4

Rivoceranib mesylate (Form A) 0.1 grams was dissolved in 4 ml of ethanol at 60-70° C. in 10 ml test tube, stirred for 5-10 minutes to obtain a clear solution. The obtained clear solution was filtered and added into the pre-chilled 10 ml of MTBE (methyl tertiary-butyl ether) or Diethyl ether, or Cyclohexane, or Hexane or Heptane (which was maintained at 0-5° C.) under magnetic stirring. The obtained slurry was maintained at 0-5° C. for 2 hours under stirring (400-500 rpm) and kept further at −5 to 5° C. for additional 2 days without stirring. The obtained solid was filtered under vacuum with nitrogen atmosphere blanket and kept suck dried for 10-15 minutes at 25-30° C. to obtain Form RT4 (0.05 grams).

Example 12. Preparation Rivoceranib Mesylate Form RT5

Rivoceranib mesylate (Form A) 0.2 grams was added into 0.3 ml of acetic acid at 20-30° C. in 5 ml vial and the obtained slurry were stirred for 24 hours at same temperature. The obtained solid was filtered under vacuum and kept suck dried for about 30-60 minutes at 25-30° C. to obtain Form RT5 (0.12 grams).

Example 13. Preparation of Rivoceranib Mesylate Form RT2

Rivoceranib mesylate (Form A) 5.0 grams was placed in 250 ml round bottom flask and added in 50 ml of water at 60° C. and the obtained slurry was stirred for 6 hours at same temperature. The obtained solid was filtered under vacuum at 25-30° C. and kept under suction for about 60 minutes to obtain Form RT2 (3.5 grams).

Example 14. Preparation of Rivoceranib Mesylate Form RT2

Rivoceranib mesylate (Form A) 70 mg was placed in 2 ml vial and added in 0.1 ml of 2-Ethoxyethanol and 1.5 ml of water at 25-30° C. and the slurry were stirred for 24 hours at same temperature. The obtained solid was filtered under vacuum at 25-30° C. and kept under suction for about 10-15 minutes and to obtain Form RT2. Form RT2 can be obtained also by this procedure when using 2-ethanol or toluene instead of 2-Ethoxyethanol (all other conditions without change).

Example 15. Preparation of Rivoceranib Mesylate Form RT5

Rivoceranib mesylate (Form A) 4.0 grams was placed in 20 ml round bottom flask and added in 10 ml of acetic acid at 25-30° C. and the obtained slurry were stirred for 6 hours at same temperature. The obtained solid was filtered under vacuum at 25-30° C. and kept under suction for about 30 minutes and to obtain Form RT5 (3.5 grams).

The invention claimed is:

1. A crystalline form of Rivoceranib mesylate designated as Form RT4, characterized by data selected from one or more of the following:
   a) an XRPD pattern having peaks at 14.8, 17.0, 20.1, 21.7 and 26.6 degrees 2-theta ±0.2 degrees 2-theta;
   b) an XRPD pattern as depicted in FIG. 6 having peaks at 14.8, 17.0, 17.5, 18.4, 19.1, 20.1, 21.7, 22.3, 26.0 and 26.6 degrees 2-theta ±0.2 degrees 2-theta; or
   c) a combination of (a) and (b).

2. The crystalline Form RT4 of Rivoceranib mesylate according to claim 1, characterized by an XRPD pattern having peaks at 14.8, 17.0, 20.1, 21.7 and 26.6 degrees 2-theta ±0.2 degrees 2-theta, and also having one, two, three, four or five additional peaks selected from 17.5, 18.4, 19.1, 22.3 or 26.0 degrees 2-theta ±0.2 degrees 2-theta.

3. The crystalline form RT4 according to claim 1, wherein the crystalline form RT4 contains 20% or less (w/w) of any solid state forms of Rivoceranib mesylate.

* * * * *